United States Patent

Jassawalla et al.

[11] Patent Number: 6,001,056
[45] Date of Patent: Dec. 14, 1999

[54] SMOOTH VENTRICULAR ASSIST DEVICE CONDUIT

[75] Inventors: Jal S. Jassawalla, Orinda; Herbert Chen, Kensington; Donald T. Shannon, Mission Viejo, all of Calif.

[73] Assignee: Baxter International Inc., Deerfield, Ill.

[21] Appl. No.: 09/191,506

[22] Filed: Nov. 13, 1998

[51] Int. Cl.⁶ .................................................. A61M 1/10
[52] U.S. Cl. ............................................................ 600/16
[58] Field of Search .............................. 600/16, 17, 18; 623/3

[56] References Cited

U.S. PATENT DOCUMENTS

| | | |
|---|---|---|
| 3,409,914 | 11/1968 | Jones . |
| 4,086,665 | 5/1978 | Poirier . |
| 4,195,623 | 4/1980 | Zeff et al. . |
| 4,222,127 | 9/1980 | Donachy et al. . |
| 4,247,292 | 1/1981 | Angell . |
| 4,581,029 | 4/1986 | Joh . |
| 4,629,459 | 12/1986 | Ionescu et al. . |
| 4,650,486 | 3/1987 | Chareire . |
| 4,759,758 | 7/1988 | Gabbay . |
| 4,759,759 | 7/1988 | Walker et al. . |
| 4,781,716 | 11/1988 | Richelsoph . |
| 4,838,889 | 6/1989 | Kolff . |
| 4,902,291 | 2/1990 | Kolf . |
| 4,925,377 | 5/1990 | Inacio et al. . |
| 5,123,919 | 6/1992 | Sauter et al. . |
| 5,129,789 | 7/1992 | Thornton et al. . |
| 5,133,744 | 7/1992 | Ramos Martinez . |
| 5,139,515 | 8/1992 | Robicsek . |
| 5,147,385 | 9/1992 | Beck et al. . |
| 5,609,626 | 3/1997 | Quijano . |

FOREIGN PATENT DOCUMENTS

| | | |
|---|---|---|
| 170262 | 2/1986 | European Pat. Off. . |
| 2619239 | 7/1977 | Germany . |
| 1593651 | 7/1987 | U.S.S.R. . |
| 1268484 | 3/1972 | United Kingdom . |
| 1315844 | 5/1972 | United Kingdom . |
| 1315845 | 5/1973 | United Kingdom . |
| 1477643 | 6/1977 | United Kingdom . |
| 2187536 | 9/1987 | United Kingdom . |
| WO 82/01647 | 5/1982 | WIPO . |
| WO 90/14804 | 12/1990 | WIPO . |
| WO 93/20757 | 10/1993 | WIPO . |

OTHER PUBLICATIONS

Vascutek, (a company of SulzerMedico) Gelsoft ERS®.
Vascutek, (a company of SulzerMedico) Gelseal®.
Vascutek, (a company of SulzerMedico) Gelweave®.

*Primary Examiner*—Scott M. Getzow
*Attorney, Agent, or Firm*—Guy L. Cumberbatch; Baxter Healthcare Corp.; Peter Jon Gluck

[57] ABSTRACT

A smooth-walled non-crimped inflow conduit for an implantable ventricular assist system. The conduit has an internally smooth lumen surface for enhanced washing of the conduit under irregular blood flow conditions. The conduit includes a tubular graft body that may be formed of a knitted fabric sealed with bovine collagen or gelatin, or formed of closed structured PTFE. The conduit may include external ribbing or support to prevent inward collapse under negative pressure conditions and also protect against damage from inadvertent physical contact in the operating room. The external support may be bonded to the exterior or formed integrally with the tubular graft body. An outer reinforcement cage may be provided to help prevent gross distortion or damage to the tubular graft body. The ends of the tubular graft body are left unsupported and wrapped around opposed lips of conduit coupling structure to minimize blood contacting surfaces at junctions with other conduits or with the heart. The conduit may be provided in an implantable left ventricular assist system also including a pumping device, valved conduits, and a power supply.

37 Claims, 7 Drawing Sheets

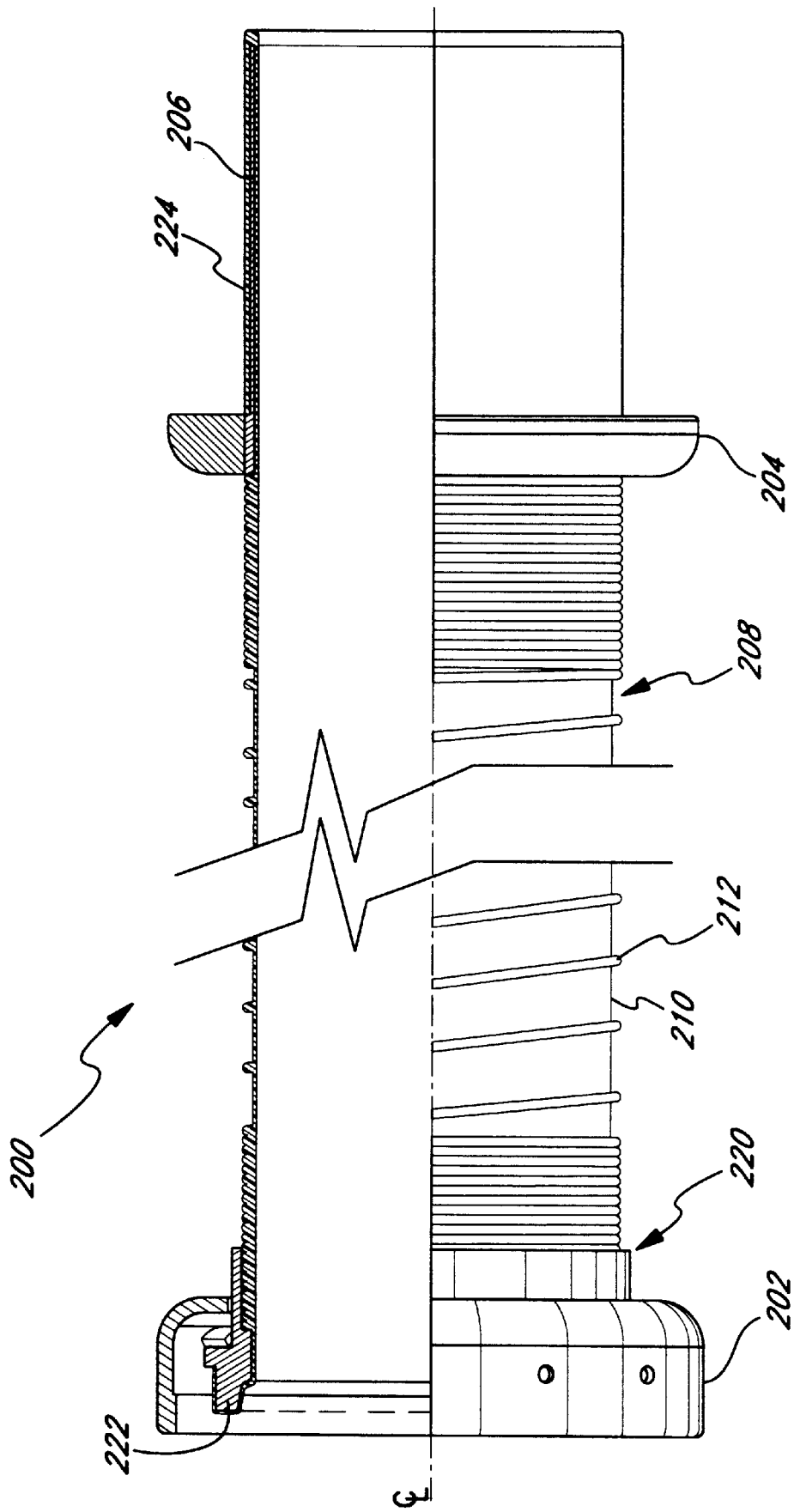

SMOOTH VENTRICULAR ASSIST DEVICE CONDUIT

BACKGROUND OF INVENTION

1. Field of the Invention

The present invention pertains to ventricular assist devices, and more particularly to artificial prosthetic conduits used for transporting blood in the circulatory system of a living organism.

2. Description of the Prior Art

More than two and one-half million Americans suffer from congestive heart failure. Most heart disease involves the left ventricle of the heart. This pumping chamber is generally known as the workhorse of the heart. A patient with a non-functioning right ventricle can survive quite successfully provided that their pulmonary blood flow resistance is low enough to allow circulation through the lungs and the rest of the body entirely as a result of the efforts of the left ventricle. However, collapse of the left ventricle is most often fatal.

Left-ventricular assist devices (LVAD) in particular are recognized as potentially very valuable for assisting patients who suffer from congestive heart failure. An LVAD is able to fully take over the function of the left ventricle, thus perfusing the body with oxygen-rich blood. The LVAD attaches to the patient's natural heart, and to a natural artery, and can be removed if the natural heart recovers. Some LVADs are surgically implanted into the patient's abdominal cavity, while others remain outside the body and are placed in fluid communication with the heart via elongated cannulas. Recently, a National Institutes of Health study estimated that as many as thirty-five thousand people could be candidates for use of a left-ventricular assist device.

At present, conventional ventricular assist devices are used for patients a) who are waiting for a heart transplant (a so-called, "bridge to transplant"), b) whose natural heart is of such poor condition that the patient cannot be removed from a heart-lung machine without providing some assistance to the patient's heart following otherwise successful open-heart surgery, and c) who suffer massive heart attacks that lead to circulatory collapse. The suitability of long-term utilization of conventional left-ventricular assist devices outside of the clinical environment remains under study.

Expansion and contraction of a variable-volume chamber typically effect blood flow in the LVAD. One-way valves associated with the inflow and outflow ports of the LVAD permit blood flow propelled by the natural left ventricle into the variable-volume chamber during expansion, and blood flow out of this chamber, usually to the ascending thoracic aorta. These one-way flow valves may be constructed as part of the LVAD itself, or may be disposed in separate blood-flow conduits attached thereto. A pair of artificial blood conduits respectively connect the inlet port of the variable-volume chamber (or the inlet end of a valved conduit) to the left ventricle and the outlet port of the variable-volume chamber (or the outlet end of a second valved conduit) to the major artery which is to receive the blood flow from the device.

As is well known, artificial blood conduits have become a valuable tool of modern medicine. One use of such artificial blood conduits is as a temporary or permanent prosthetic artery. Another use is in the connection of temporary blood pumps, such as ventricular assist devices described herein, between the left ventricle of the heart and a major artery.

The demands on artificial blood conduits in ventricular assist devices are great. The conduit must deal with the pulsatile blood flow created by the host's own heart, as well as with the flow, pressure, and pulsations created by the assist device. Moreover, there are differences in flow and pressure between the inflow and outflow conduits connected to the pumping device. For example, while the outflow conduit experiences regular pulses of high pressure, flow in the inflow conduit is dependent on the pumping strength and rhythrm of the natural left ventricle on top of which the periodic LVAD pressures are superimposed (i.e., expansion of the variable volume chamber tends to pull fluid from the inflow conduit). The inflow conduit thus sees irregular and typically low flows and pressures; indeed, negative pressure transients can occur in the inflow conduit.

Conventional artificial conduits for use in LVADs may be constructed of an elongate flexible woven polyethylene terephthalate fabric tube. In some cases, the conduits are sealed with a thin bio-compatible collagen coating on the inner lumen wall to render the fabric more leak resistant at the time of implantation, and also more compatible with the patient's blood. The collagen coating, typically bovine collagen, eventually is absorbed into the blood stream and is replaced with a natural coating of blood cells, serum protein, and other elements from the blood. In the absence of a sealant, the conduit may have to be pre-clotted by the surgeon just prior to implantation. The woven fabric tubes for implanted LVADs are invariably convoluted (crimped) to facilitate bending and extension during implantation to fit different anatomical configurations. That is, the pumping device must reside with the lower abdominal cavity and attach via the conduits to appropriate locations on the heart, none of which are precisely the same in each patient. The convoluted conduits accommodate this variability without kinking. A conventional artificial blood conduit is disclosed in U.S. Pat. No. 5,810,708, issued Sep. 22, 1998, to Woodard.

Some non-implantable ventricular assist-devices utilize cannula-like conduits that are relatively rigid, some being fonned of smooth, reinforced polyurethane. These types of conduits would not be suitable for use in implantable devices as they will not easily accommodate varying anatomical placements, and tend to kink if bent. In addition, smooth-walled woven fabric grafts are relatively stiff, and tend to kink when bent.

In spite of extended efforts in the industry, there remains room for improvement in the construction and function of conduits for ventricular assist devices.

SUMMARY OF THE INVENTION

The present invention provides an inflow conduit for an implantable ventricular assist device comprising a flexible tubular graft body having an upstream end and a downstream end, the body having a substantially smooth inner surface for enhanced flow-through of blood with a minimum of surface-induced turbulence. The inflow conduit includes a ventricular attachment structure to which the upstream end of the body connects, and a coupling fitting on the downstream end of the body. Desirably, the tubular graft body is a knitted fabric, preferably a polyethylene terephthalate fabric having a biocompatible sealant impregnated therein. The sealant may be bovine gelatin or bovine collagen. Alternatively, the tubular graft body is made of closed structured PTFE to resist tissue ingrowth.

In another aspect, the present invention provides a ventricular assist device inflow conduit comprising a flexible tubular graft body having a smooth inner surface and an external kink-resistive supporting structure, the graft having opposed ends. The inflow conduit includes a ventricular attachment structure on one end of the tubular graft body and a coupler fitting on the other end. Desirably, the supporting structure comprises a helically wound coil. The helically wound coil may be wound tighter at the opposed ends of the tubular graft body than in the middle portion, and is preferably polypropylene or PTFE thermally bonded to the external surface of the tubular graft body.

In still another aspect, the present invention provides a ventricular assist device inflow conduit comprising a flexible tubular graft body having an upstream end and a downstream and a smooth, non-convoluted interior lumen. The inflow conduit includes a ventricular attachment structure on the upstream end of the graft including a tubular cannula portion having a distal rim for extending into the ventricle. An external apical ring about the tubular cannula portion and spaced from the distal rim enables sewing to the external ventricle wall. The upstream end of the graft extends through the cannula portion and is wrapped around the distal rim to lie against the exterior of the cannula portion and attach to the apical ring.

The present invention also provides an implantable ventricular assist device comprising an inflow conduit including a flexible tubular graft body having an upstream end and a downstream end, the body having a substantially smooth inner surface for enhanced flow-through of blood with a minimum of surface-induced turbulence. The inflow conduit also includes a ventricular attachment structure to which the upstream end of the body connects, and a coupling fitting on the downstream end of the body. An implantable pumping portion is placed in flow communication with the inflow conduit and with an outflow conduit. The tubular graft body may be a knitted fabric having a biocompatible sealant impregnated therein, or a closed structured PTFE to resist tissue ingrowth.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

FIG. 7 is a partial sectional view of the inflow conduit of FIG. 6.

DETAILED DISCUSSION OF THE PREFERRED EMBODIMENT(s)

Figure 1:
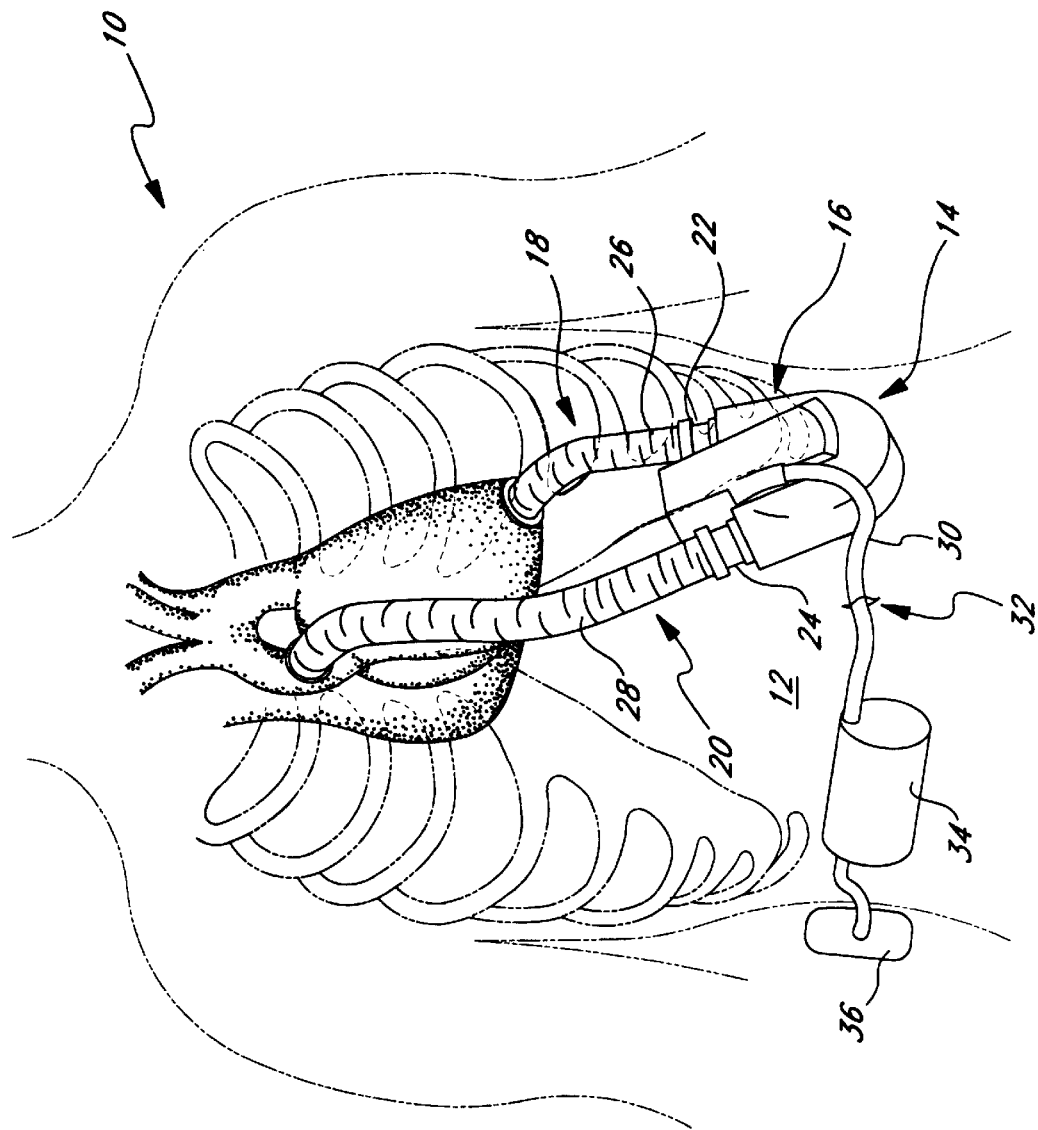
FIG. 1 is a front view of a left ventricular assist system of the present invention connected to a heart of a patient (shown in phantom)

With reference first to FIG. 1, a living human host patient 10 is shown in fragmentary front elevational view, and with parts of the patient's anatomy shown in phantom or removed solely for better illustration of the salient features of the present invention. It will be understood that the human host patient 10 preferably has a complete anatomy, and that the use of the present invention does not generally require that any part of the patient's normal anatomy be removed, as might be suggested by FIG. 1.

Surgically implanted into the patient's abdominal cavity 12 is the pumping portion 14 of a ventricular assist device, generally referenced with the numeral 16. The ventricular assist device 16 includes a valved inflow conduit 18 communicating blood from the patient's left ventricle into the pumping portion 14, and a valved outflow conduit 20 communicating blood from the pumping portion 14 to the patient's ascending thoracic aorta.

Figure 2:
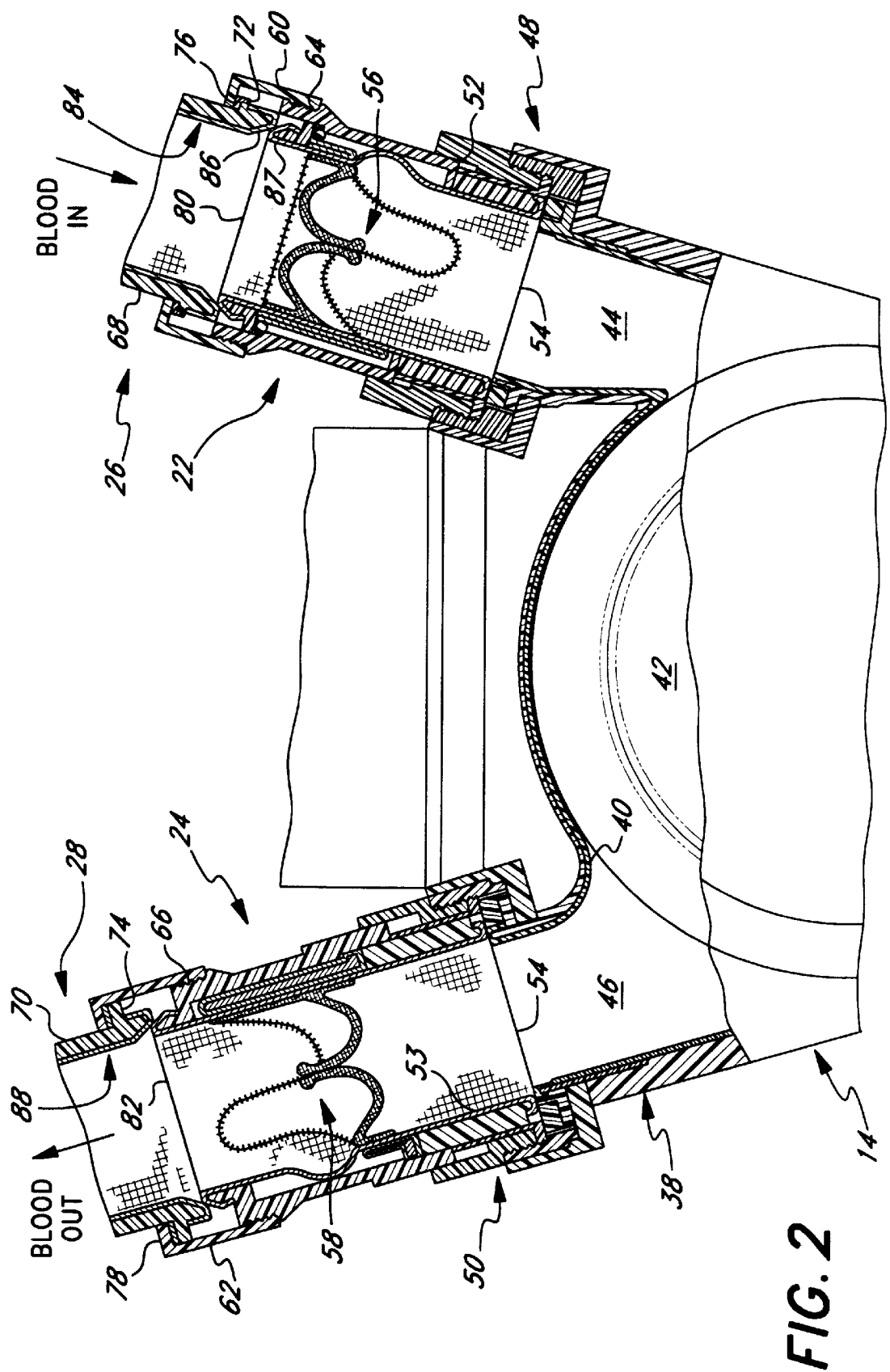
FIG. 2 is a partial cross-sectional view of a left ventricular assist device connected to inflow and outflow conduits of the present invention.

As seen in FIGS. 1 and 2, the conduits 18, 20 typically comprise short valved segments 22, 24 proximate the pumping portion 14 of the device connected in series to elongated flexible segments 26, 28 extending to the heart and ascending aorta, respectively. At the end of the inflow conduit 18 which is connected to the patient's heart, and at the end of the outflow conduit 20 which is connected to the ascending thoracic aorta, these conduits are attached to the natural tissues by sutures so that blood flow communication is established and maintained. From the pumping portion 14 a power cable 30 extends outwardly of the patient's body via an incision 32 to a compact controller 34. A power source, such as a battery pack worn on a belt about the patient's waist, and generally referenced with the numeral 36, is connected with the controller 34. Other means for powering the LVAD 16 are known which do not require a cable through the skin, and the present invention is not so limited.

Viewing FIG. 2, it is seen that the pumping portion 14 includes a housing 38 within which is received a flexible unitary liner or bag member 40. This bag member 40 defines a singular blood-contacting inner surface, bounding a variable-volume chamber 42. The bag member 40 includes a diaphragm portion (not shown) which is reciprocally movable in response to reciprocating movements of a power member (not shown) of the pumping portion 14 to expand and contract the variable-volume chamber 42. It should be noted that though variable-volume chamber pumps currently predominate in LVAD designs, there is research ongoing into the substitution of rotary-type pumps. As FIG. 2 illustrates, the bag member 40 also defines tubular leg portions 44, 46, extending to and through respective inlet and outlet fittings 48, 50 of the housing 38. At the inlet and outlet fittings 48 and 50, the housing 38 includes structural provisions allowing connection and disconnection of the respective inflow and outflow conduits 18, 20, as will be further described.

Importantly, as FIG. 2 shows, each of the valved inflow and outflow conduit segments 22, 24, respectively includes a tubular flexible, but shape-retaining fabric-composite inner wall member 52, 53 having an inner blood-contacting surface. As will be further explained, the inner blood-contacting surfaces of the valved conduit segments 22 and 24 each also defines a respective reentrant end portion which sealingly contact the reentrant portions of the bag member 40. These sealingly contacting reentrant portions cooperatively define sealing lines 54. Consequently, the flowing blood in moving from the inflow valved conduit segment 22 to the bag 40, and from this bag to the outflow valved conduit segment 24, crosses only two material-surface transitions. The first of these material-surface transitions is from the surface of the inner wall member 52 at the inflow conduit segment 22 to the inner surface of the bag 40, and the second of these material-surface transitions is from the inner surface of the bag 40 to the inner wall member 53 at the outflow conduit segment 24. As is described in detail in U.S. Pat. No. 5,810,708, hereby expressly incorporated by reference, this minimizing of material-surface transitions which are exposed to flowing blood in the ventricular assist device 16 is a consistent feature throughout the device.

The valved segments 22, 24 of the inflow and outflow conduits 18, 20 both contain one way valves 56, 58 respectively. In a preferred embodiment, the valves 56, 58 comprise excised xenograft valves from, for example, pigs. In addition, the tissue valves preferably have a length-to-diameter aspect ratio greater than natural valves which improves flow therethrough. Again, this preferred arrangement is described in detail in U.S. Pat. No. 5,810,708. Although the present inflow conduit 18 is described as a flexible conduit segment connected to a short valved conduit segment, it will be appreciated by those of skill in the art that the inventive aspects disclosed herein could be applied to a combined single segment flexible valved conduit. Indeed, the one-way valves 56, 58 require a smooth inner conduit wall surface for proper attachment and operation, which, as will be described, is provided by the novel flexible segment 26 of the present invention.

FIG. 2 illustrates the connection between the valved segments 22, 24 and the elongate flexible segments 26, 28 of the inflow and outflow conduits. More particularly, each of the flexible segments 26, 28 carries a coupler fitting 60, 62 thereon having internal threads for mating with external threads 64, 66 provided on the respective valved segments 22, 24. The fittings 60, 62 are captured on and rotate relative to tubular rigid bodies 68, 70, each of which includes outwardly extending flanges 72, 74. The coupler fittings 60, 62 include inwardly directed radial walls 76, 78 which interfere with the flanges 72, 74. With this arrangement, the flexible segments 26, 28 secure to the valved segments 22, 24 by threading the coupler fittings 60, 62 over the external threads 64, 66.

As in U.S. Pat. No. 5,810,708, the preferred ventricular assist device 16 of the present invention provides a minimum of blood contacting surfaces throughout the inflow conduit 18, pumping portion 14, and outflow conduit 20. At the respective junctions between the valved segments 22, 24 and flexible segments 26, 28, a single sealing line 80, 82 is defined between the innermost linings of the juxtaposed segments. More specifically, the flexible segment 26 of the inflow conduit 18 includes an inner lining 84 which is wrapped around the end of the rigid body 68 closest to the valved segment 22, as indicated at 86. The inner wall member 52 of the valved segment 22 is wrapped around the facing end in a like manner, as seen at 87, so that the two blood contacting surfaces meet at the sealing line 80. A similar arrangement is provided between an inner lining 88 of the flexible segment 28, and the inner wall member 52 of the valved segment 24, resulting in the blood sealing line 82.

In order to more completely understand the advantages of the present invention, a flexible segment of an inflow conduit 100 of the prior art will be described with reference to FIG. 3. As mentioned previously, the flexible segment 100 on one end includes a rigid ring-shaped body 102 surrounded by coupler fitting 104. A wave washer 106 is disposed between an inwardly extending radial wall 108 of the fitting 104, and the flange 110 of the rigid body 102. The wave washer 106 produces a relatively constant compressing force at the blood sealing line formed between the flexible segment 100 and associated valved conduit segment (not shown).

The rigid body 102 is integral formed with a reinforcement cage 112 that extends the length of the flexible portion of the conduit segment 100 and terminates in a rigid band 114. The reinforcement cage 112 includes a plurality of circumferentially formed ribs 116 joined at periodic locations by bridges 118. Although not shown well in FIG. 3, the bridges 118 are circumferentially offset from each other from rib-to-rib to enable the reinforcement cage 112 to be axially extended (this is better seen in the conduit segment of the present invention seen in perspective in FIG. 4). That is, the cage 112 is desirably formed of a resilient biocompatible material such as polypropylene, and axial elongation of the segment 100 is permitted by virtue of the ribs 116 bending to enlarge the axial spaces 120 therebetween. As will be appreciated, the term "rigid" referring to the body 102 and band 114 is defined relative to the flexibility of the intermediate ribs 116, and those of skill in the art will recognize that polypropylene has inherent resiliency and is not "rigid" in the abstract. The body 102 and band 114 are desirably as rigid as needed to facilitate structural connection of the cage 112 to the respective ends of the segment 100. The body 102 and band 114 also provide a "handle" of sorts to assist the surgeon in attaching the segment 100 between the heart and associated short valved conduit.

The reinforcement cage 112 helps prevent gross distortion or collapse of a convoluted tubular graft body 122 extending therethrough. Nevertheless, extension of the flexible segment 100 during implantation of an associated ventricular assist device may cause excessive spaces to be formed between the ribs of the reinforcement cage 112. In such cases, there is the potential for the surgeon to contact the tubular graft body 122 within the reinforcement cage 112 with a finger or other instrument, resulting in damage or collapse.

The convoluted tubular graft body 122 extends from a first end 124 to a second end 126. The first end 124 is wrapped tightly around the rigid body 102, as previously described, the convolutions being smoothed at that end by a thermo-forming process. Stitching 128 surrounds the first end 124 and attaches the graft body 122 to the rigid body 102. The second end 126 extends through a rigid, tubular cannula body 130 and terminates at a distal rim 132 thereof. A smooth piece of fabric 134 surrounds the tubular cannula body 130 and is attached at the distal rim 132 to the second end 126 using a stitch line 136. At its opposite end the fabric 132 terminates at an apical sewing ring 140. The sewing ring 140 includes an inner sponge-like member 142 an outer fabric covering 144. The fabric 134 attaches to the outer fabric cover 144 of the sewing ring at a stitch line 146. Finally, the outer fabric covered 144 of the sewing ring is secured to the tubular graft body 122 via plurality of periodic discrete stitches 152, as seen in the lower portion of FIG. 3.

The tubular cannula body 130 is sized to extend within an excised opening at the apex of the left ventricle. In this regard, therefore, the end of the flexible segment 100 having the tubular cannula body 130 is considered the "upstream" end, and the opposite end having the coupler fitting 104 is the "downstream" end.

As mentioned above, flow patterns in the inflow conduit side of a ventricular assist device are highly variable, and may even induce negative pressures. The convoluted tubular graft body 122 of the prior art, as seen in FIG. 3, is advantageous for its high flexibility and capacity for elongation. In addition, the convoluted tubular graft body 122 has a relatively high resistance to kinking upon bending. On the other hand, negative pressures generated within the flexible segment of inflow conduit 100 may cause unwarranted narrowing or inward distortion of the tubular graft body 122. In addition, the convolutions may induce undesirable eddy currents near the wall of the tubular graft body and the inner concave portions of the convolutions may provide blood stagnation sites, further encouraging undesirable thrombotic depositions. Furthermore, the convolutions of the tubular graft body 122 are unsuitable for wrapping around the cannula body 130, as the exterior surface thereof must pass cleanly through and seal against the excised opening at the apex of the left ventricle. Therefore, the separate piece of fabric 134 having a smooth construction is needed. This increases the time and expense of assembly of the flexible segment 100.

Figure 3:
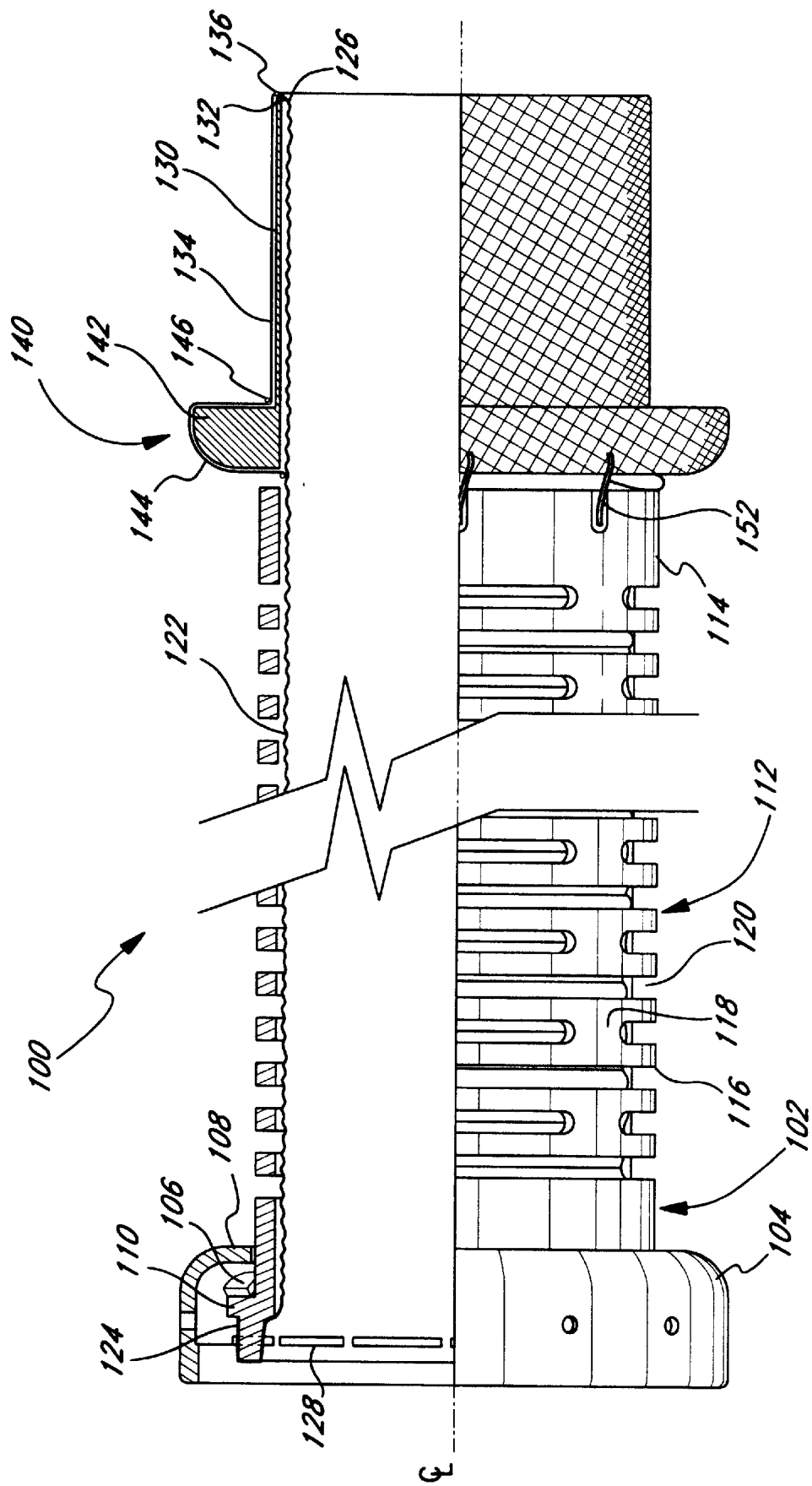
FIG. 3 is a partial sectional view of an inflow conduit of the prior art.
Figure 4:
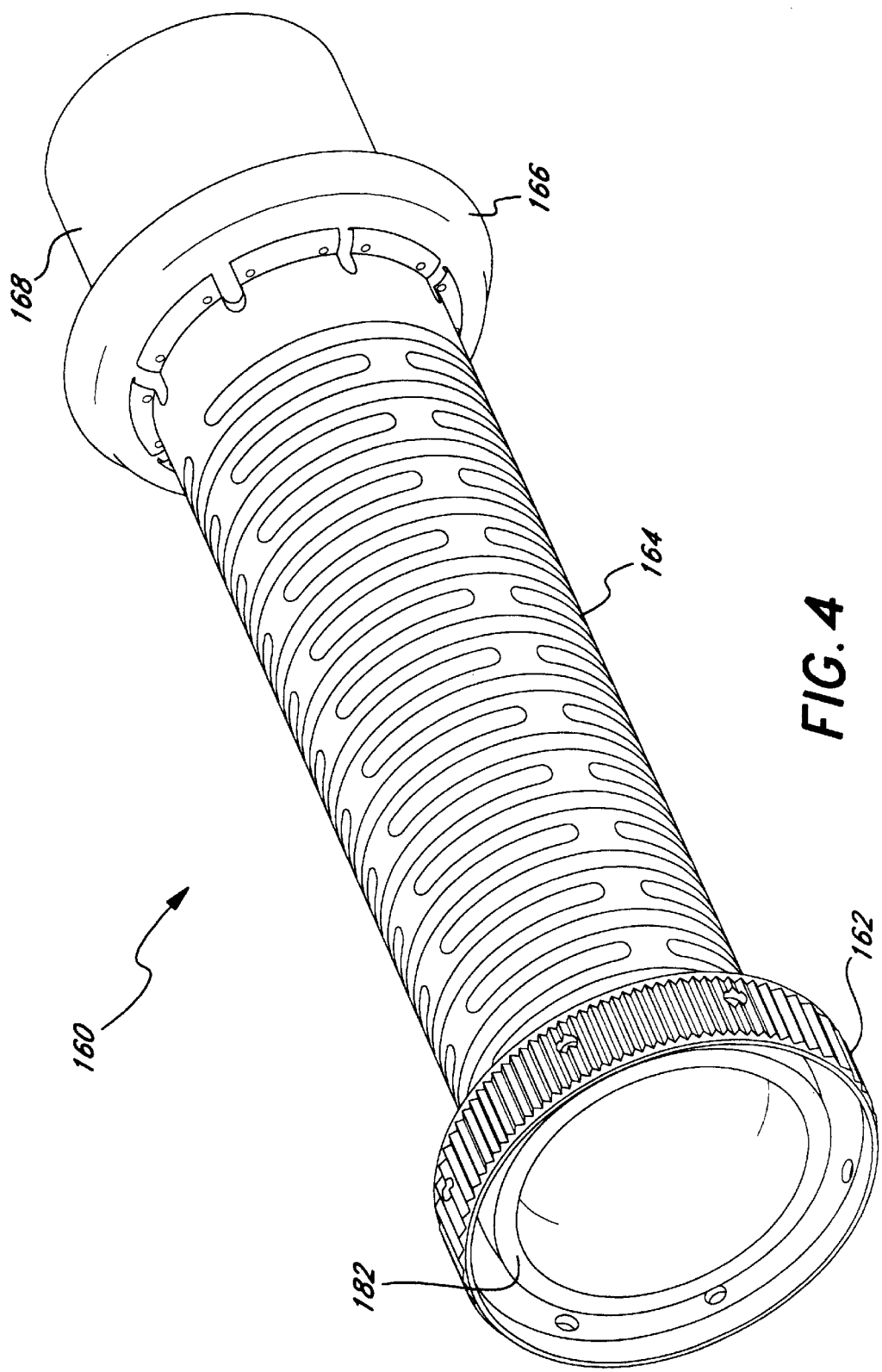
FIG. 4 is a perspective view of an inflow conduit of the present invention.
Figure 5:
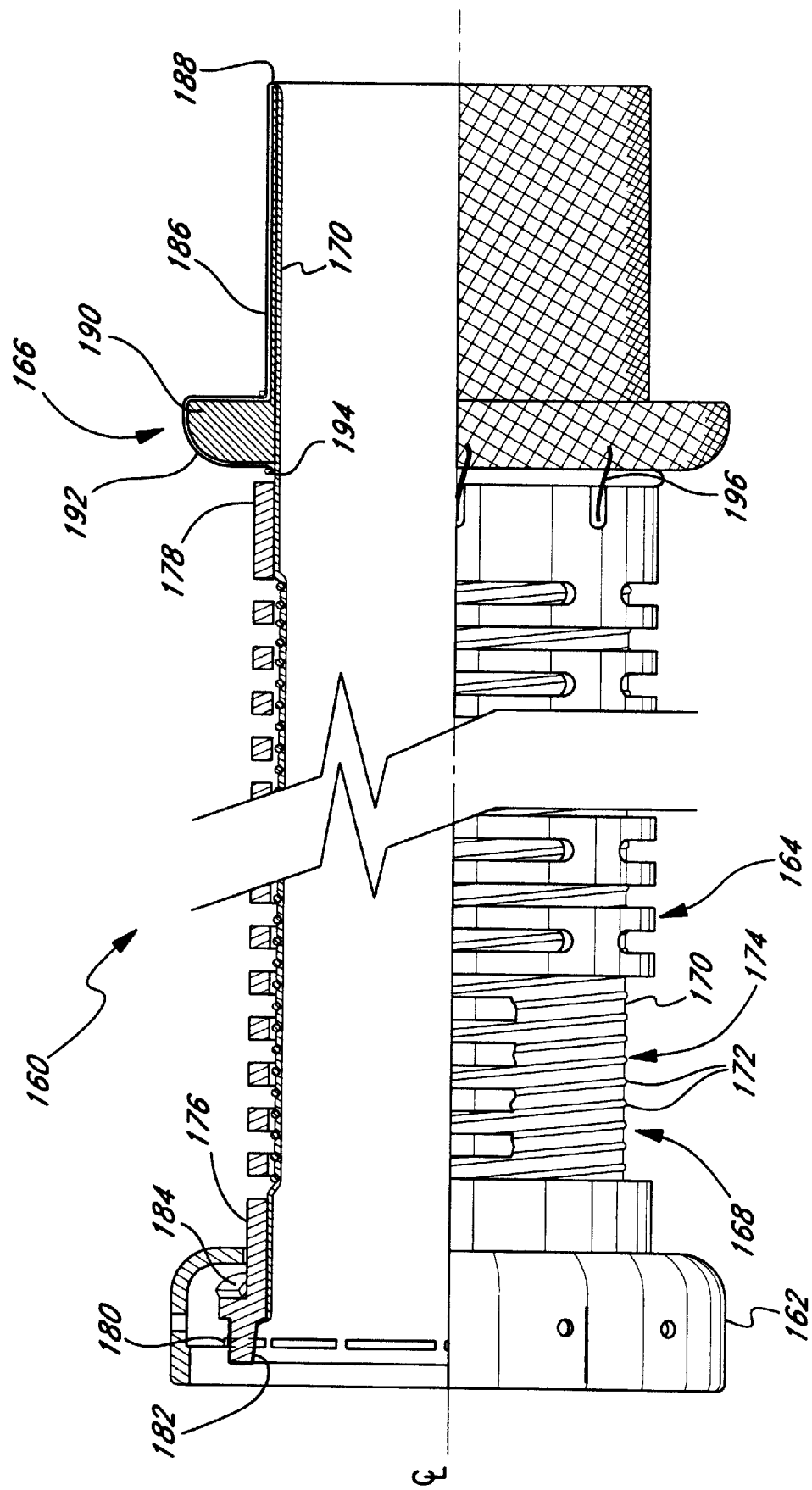
FIG. 5 is a partial sectional view of the inflow conduit of FIG. 4.

FIGS. 4 and 5 illustrate an improved flexible segment 160 for an inflow conduit 18 (FIG. 1) of a ventricular assist device 16. The flexible segment 160 shares certain features with the flexible segment 100 of the prior art shown in FIG. 3. Namely, the flexible segment 168 includes a coupler fitting 162, reinforcement cage 164, a sewing ring 166, and a tubular cannula body 186 (FIG. 5). In contrast to the prior art, the cannula body 186 is covered by a portion of an improved tubular graft body 168 as will be described.

It should be noted here that the outflow conduit 20 of FIGS. 1 and 2 for use in conjunction with the inflow conduit of the present invention remains essentially unchanged from that of the prior art. That is, the flexible segment 28 preferably includes a convoluted tubular graft body of woven polyethylene terephthalate fabric protected by an outer reinforcement cage (much like the prior art inflow conduit of FIG. 3). The fabric may be impregnated with a natural sealant, such as bovine collagen or bovine gelatin.

FIG. 5 illustrates the improved tubular graft body 168 for the inflow conduit 18 (FIG. 1) extending through and defining the inner lumen of the flexible segment 160. More specifically, the tubular graft body 168 includes an internally smooth, non-crimped flexible wall 170 and a plurality of axially spaced support members 172 around the exterior of the wall. Desirably, the support members 172 comprise individual coils of a single helically wound support member 174. The support member 174 extends axially within the reinforcement cage 164 between a rigid body portion 176 and a rigid band 178, while the flexible wall 170 continues axially outward to both ends of the tubular graft body 168 as will be described.

In a preferred embodiment, tubular wall 170 comprises a knitted fabric sealed by a bovine collagen or bovine gelatin. Knitted fabrics for such uses typically have larger pore sizes and are significantly more flexible than woven fabrics. The large pore sizes necessitate the use of a sealant. Because of the flexibility of the knitted structure, however, the tubular wall 170 may be bent a substantial degree, more so than woven tubes, without undesirable kinking. Moreover, elimination of the convolutions in tubular graft bodies of the prior art reduces the potential for thrombosis and hemolysis. That is, the smooth inner surface of the tubular wall 170 facilitates washing of the tubular wall under conditions of transient or low blood flow. Blood passes through the lumen of the tubular wall 170 such that there are no discontinuities or cavities to collect stagnant blood. "Smooth" in the context of the improved inflow conduit segment 160 means that the inner lumen of the tubular wall 170 is relatively cylindrical and free of convolutions.

The external support member 174 may be formed in a variety of configurations, including the helically wound circular cross-section as shown. Various other reinforcing techniques for tubular grafts are known in the art, including, but not limited to discrete bands, adhered ribs, wound tape, and the like. In a particularly preferred embodiment, the support member 174 comprises a helical polymer coil, preferably polypropylene, thermally bonded to the exterior surface of tubular wall 170. Other biocompatible materials capable of being thermally bonded or otherwise adhered to the exterior surface of tubular wall 170 may be used for the support member 174, including PTFE. The support member 174 prevents the tubular wall 170 from collapsing inward, yet without significantly affecting the flexibility thereof. In addition, the external support member 174 surrounding the tubular wall 170 helps protect the tubular graft body 168 from damage from inadvertent contact upon extension of the flexible segment 160. That is, during implantation of an associated ventricular assist device excessive spaces may be formed between the ribs of the reinforcement cage 164 from elongation of the flexible segment 160. In such cases, the surgeon might inadvertently contact the tubular graft body 168 within the reinforcement cage 164 with a finger or other instrument. The support member 174 protects the tubular wall 170 from collapse or damage.

A particularly preferred tubular graft body 168 including a sealed, smooth tubular wall 170 having a bore diameter of about 22 mm and a helically wound external support member 174, may be obtained on special order from Vascutek of Inchinnan, Scotland, under the trade name GELSEAL ERT®.

As in the previously described flexible segment of the prior art seen in FIG. 3, the tubular graft body 168 extends around the downstream end of the rigid body member 176 and is sewn thereto with a line of stitches 180. This construction presents a coupling surface 182 as seen in FIG. 4 which is designed to mate with a complementary coupling surface of a valved conduit segment. The tubular wall 170 thus forms the "lining 84" as previously denoted with respect to FIG. 2. In addition, a wave washer 184 (FIG. 5) creates a relatively constant compressive force between the mating coupling surfaces.

On the upstream end of the flexible segment 160, the tubular wall 170 wraps around a distal rim 188 of the tubular cannula body 186 and continues into proximity with the sewing ring 166. Again, the sewing ring includes an inner sponge-like portion 190 surrounded by a fabric covering 192. The fabric covering 192 is sewn to the tubular graft body 168 using, for example, stitches 194. Additionally, the sewing ring 166 attaches to the reinforcement cage 164 using stitches 196. The use of a smooth-walled tubular graft body 168 eliminates the need for a separate piece of fabric surrounding the cannula body 186, such as the prior art fabric piece 134 seen in FIG. 3.

Figure 6:
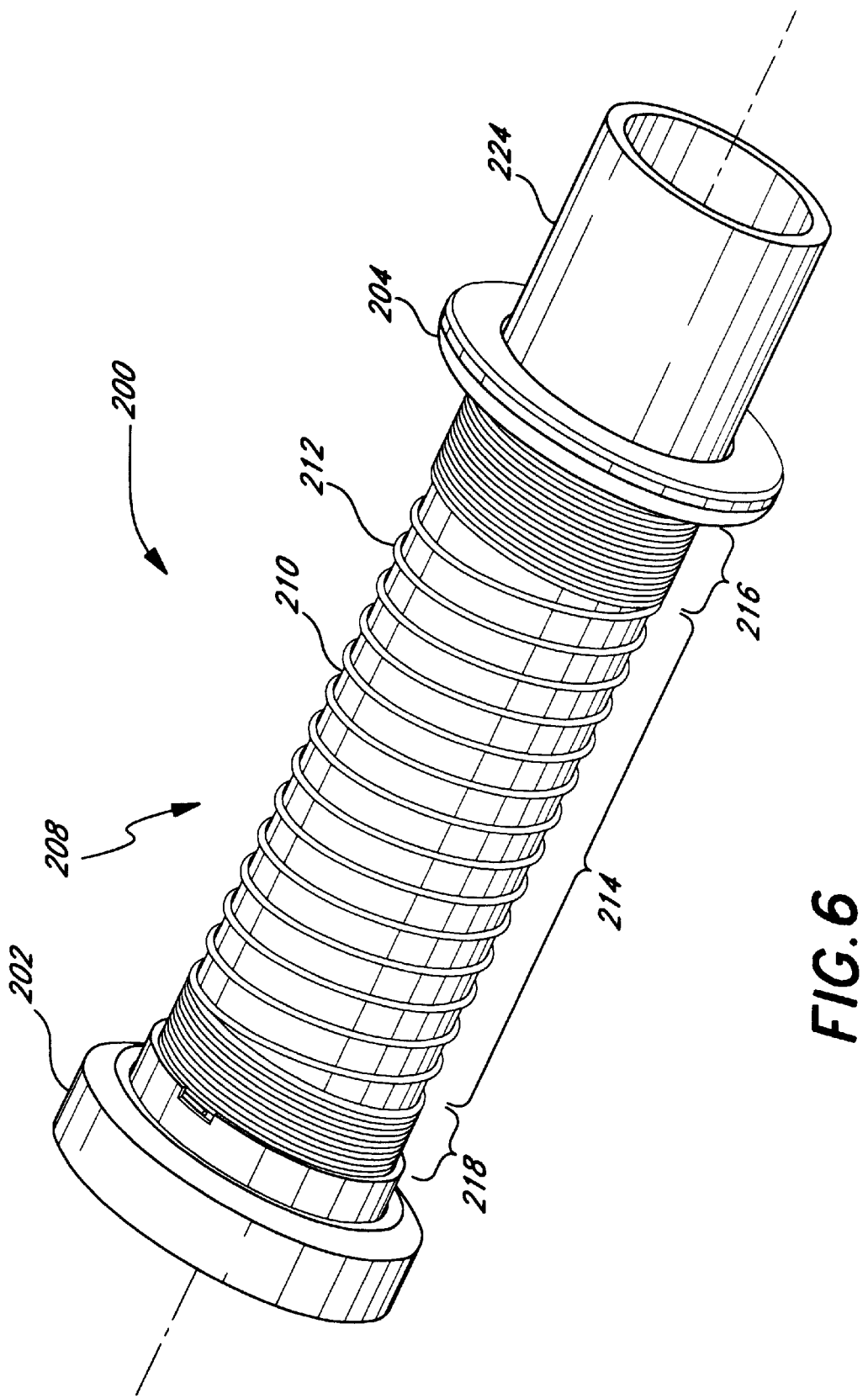
FIG. 6 is a perspective view of a further embodiment of an inflow conduit of the present invention.

FIGS. 6 and 7 illustrates a second embodiment of a smooth-walled, non-crimped flexible segment 200 for an inflow conduit of a ventricular assist device. As before, the flexible segment 200 has a downstream end with a coupler fitting 202 and an upstream end with a sewing ring 204 and a tubular cannula body 206. In contrast to the previously described embodiment, there is no reinforcement cage. Instead, a tubular graft body 208 comprises a flexible tubular wall 210 and a plurality of external reinforcing members 212. As will be described, the material and construction of the tubular graft body 208 is sufficiently flexible while at the same time being sufficiently able to withstand collapse, so as to obviate the need for the reinforcement cage.

In a preferred embodiment, tubular graft body 208 is formed of a closed structure polytetrafluoroethylene (PTFE). A smooth PTFE graft body 208 without convolutions is particularly useful in the context of the inflow conduit for a ventricular assist device because it reduces the tendency to induce irregular flow patterns. "Smooth" in the context of the improved inflow conduit segment 200 means that the inner lumen of the graft body 208 is at least free of convolutions, though it will be noted that the surface smoothness of a PTFE graft body is dependent on the smoothness of the extrusion forming mandrel. Indeed, the mandrel is desirably highly polished resulting in an extremely smooth inner lumen of the tubular graft body 208. Moreover, closed structured PTFE significantly reduces tissue ingrowth from the exterior or ends of the tubular graft body 208 which otherwise might eventually encroach on the inner lumen and initiate a thrombotic response.

As mentioned, the external reinforcing members 212 of the flexible segment 200 in FIGS. 6 and 7 obviate the need for a reinforcement cage, such as the cage 164 of FIG. 5, which reduces the difficulty associated with explant surgery of the LVAD. More particularly, host tissue tends to encapsulate the reinforcement cage 164 of the segment 160 of FIG. 5 after a period of implantation. When the LVAD is to be removed from the patient, the surrounding tissue ingrowth must be carefully cut away, which is complicated by the intricate nature of the reinforcement cage 164. The PTFE tubular graft body 208 of the flexible segment 200 in FIGS. 6 and 7 has no surrounding protective cage, and is thus much easier to remove from the patient once the need for the LVAD ceases.

The external reinforcement members 212 may comprise a series of coils of a continuous rib having a circular or semi-circular cross-section projecting outward from the tubular wall 210. The reinforcement coils 212 extend generally between the coupler fitting 202 and sewing ring 204 and are preferably axially spaced apart in a mid-region 214 while being more tightly spaced (even in contact) at upstream and downstream regions 216, 218, respectively. The loosely spaced mid-region 214 permits the segment 200 to bend, and the tightly spaced regions 216, 218, provide rigidity to the flexible segment 200 in the areas adjacent the associated coupling structures (i.e., the fitting 202 and the sewing ring 204). This helps the surgeon in connecting the flexible segment 200 in its proper place, and takes the place of the rigid bands formed on either end of the reinforcement cage in the first embodiment of FIGS. 4 and 5.

With reference to cross sectional view of FIG. 7, the flexible conduit segment 200 additionally includes a rigid body portion 220 on the downstream end of the tubular graft body 208. This rigid body portion 220 provides an interface with the coupler fitting 202, and also provides a terminal lip 222 around which is wrapped the downstream end of the tubular wall 210 to form a surface for contacting a like surface on the associated valved conduit, thus minimizing the number of blood contacting surfaces across the transition. The tubular wall 210 thus forms the "lining 84" as previously denoted with respect to FIG. 2. On the opposite, upstream end of the flexible segment 200, the tubular wall 210 wraps around the tubular cannula body 206 at outer section 224 and attaches to the sewing ring 204. Again, this eliminates the need for a separate piece of fabric or other such covering around cannula body 206.

The PTFE tubular wall 210 and external reinforcement members 212 may be formed by various means well-known in the art, such as, for example, extrusion followed by expansion. In a particularly preferred method, the tubular wall 210 comprises an extruded PTFE base tube with a thin external tape wrapped around it and laminated thereto for hoop strength. The reinforcement members 212 preferably comprise a bead helically wrapped around the tubular wall 210 and also laminated thereto.

In a particular preferred embodiment, the tubular wall 210 has a thickness of about 0.7 mm. The reinforcing coils 212 may be circular in cross section having a diameter of about 1.6 mm, and extend radially outward from the tubular wall 210 a distance of approximately 1.6 mm (i.e., a circular bead on the exterior of the tubular wall 210). For better conformity, the coils 212 have a flat or groove on the side in contact with the tubular wall 210 to reduce the undercuts formed on the longitudinal edges of a wholly circular bead.

To produce a closed structured PTFE, the base tube of the tubular wall 210 desirably has a pore size of less than 20 μm, and preferably less than about 15 μm, potentially down to about 2 μm. In addition, the water entry pressure for the base tube is at least about 5 psi. A thin PTFE tape wrapped about and laminated to the base tube preferably has a thickness of about 0.01 mm and an ethanol bubble point of at least about 2 psi, further exhibiting no measurable nodal formations. The result is an extremely low porosity tubular wall 210 that resists tissue ingrowth therethrough and also resists endothelial cell formation therealong that may otherwise tend to migrate into the flow passage from the ends of the conduit 200.

In a still further embodiment that combines some of the features of the conduit segments 160 and 200 of FIGS. 5 and 7, respectively, a sealed fabric graft may be adequately supported by external beading so as to eliminate the need for a reinforcement cage. More specifically, this hybrid conduit segment (not shown) may include a tubular wall (such as wall 170 in FIG. 5) of a knitted fabric sealed by bovine gelatin and supported by a coil (such as external reinforcing members 212 of FIG. 7) of sufficient rigidity to adequately prevent inward collapse of the conduit segment from negative lumen pressures. Desirably, the coil would be more tightly wound at the ends than in the middle so as to facilitate handling by the surgeon yet not impede overall flexibility of the conduit to any great extent. Various combinations of fabric and coil are contemplated, including a preferred combination of a PTFE coil bonded to a polyethylene terephthalate fabric tube. Furthermore, as mentioned above, support structure other than a coil may be used, such as tape, rings, or other similar expedients.

The present invention may be embodied in other specific forms without departing from its spirit or essential characteristics. The described embodiments are to be considered only as illustrative and not restrictive. The scope of the invention is, therefore, indicated by the appended claims rather than by the foregoing description. All changes that come within the meaning and range of equivalency of the claims are to be embraced within their scope.

We claim:

1. An inflow conduit for an implantable ventricular assist device, comprising:
   a flexible tubular graft body having an upstream end and a downstream end, the body having a substantially smooth inner surface for enhanced flow-through of blood with a minimum of surface-induced turbulence;
   a ventricular attachment structure to which the upstream end of the body connects; and
   a coupling fitting on the downstream end of the body.

2. The inflow conduit of claim 1, wherein the tubular graft body is a knitted fabric.

3. The inflow conduit of claim 1, wherein the tubular graft body is a polyethylene terephthalate fabric.

4. The inflow conduit of claim 1, wherein the tubular graft body is a fabric having a biocompatible sealant impregnated therein.

5. The inflow conduit of claim 4, wherein the sealant is bovine gelatin.

6. The inflow conduit of claim 4, wherein the sealant is bovine collagen.

7. The inflow conduit of claim 1, further including an external support secured to an external surface of the tubular graft body.

8. The inflow conduit of claim 7, wherein the external support comprises a helically wound coil.

9. The inflow conduit of claim 7, wherein the external support comprises a helically wound polypropylene coil thermally bonded to the external surface of the tubular graft body.

10. The inflow conduit of claim 1, wherein the tubular graft body is made of PTFE.

11. The inflow conduit of claim 11, wherein the PTFE is closed structured to resist tissue ingrowth from the exterior of the tubular graft body.

12. The inflow conduit of claim 10, further including a plurality of reinforcement members secured to an external surface of the tubular graft body.

13. The inflow conduit of claim 12, wherein the plurality of reinforcement members are fonned by a helically wound coil.

14. The inflow conduit of claim 13, wherein the helically wound coil is wound tighter at the opposed ends of the tubular graft body than in the middle portion.

15. The inflow conduit of claim 1, wherein the ventricular attachment structure on the upstream end of the graft includes a tubular cannula portion having a distal rim for extending into the ventricle, and an external apical ring spaced from the distal rim for sewing to the external ventricle wall, the upstream end of the graft extending through the cannula portion and being wrapped around the distal rim to lie against the exterior of the cannula portion and attach to the apical ring.

16. An inflow conduit for an implantable ventricular assist device, comprising:
   a flexible tubular graft body having a smooth inner surface and an external kink-resistive supporting structure, the graft having opposed ends;
   a ventricular attachment structure on one end of the tubular graft body; and
   a coupling fitting on the other end of the tubular graft body.

17. The inflow conduit of claim 16, wherein the tubular graft body is a fabric having a biocompatible sealant impregnated therein.

18. The inflow conduit of claim 16, wherein the tubular graft body is made of closed structured PTFE to resist tissue ingrowth from the exterior of the tubular graft body.

19. The inflow conduit of claim 16, wherein the supporting structure comprises a helically wound coil.

20. The inflow conduit of claim 19, wherein the helically wound coil is wound tighter at the opposed ends of the tubular graft body than in the middle portion.

21. The inflow conduit of claim 19, wherein the helically wound coil is polypropylene thermally bonded to the external surface of the tubular graft body.

22. The inflow conduit of claim 19, wherein the helically wound coil is PTFE bonded to the external surface of the tubular graft body.

23. The inflow conduit of claim 19, wherein the helically wound coil is formed integrally with the tubular graft body.

24. An inflow conduit for an implantable ventricular assist device, comprising:
   a flexible tubular graft body having an upstream end and a downstream and a smooth, non-convoluted interior lumen; and
   a ventricular attachment structure on the upstream end of the graft including a tubular cannula portion having a distal rim for extending into the ventricle, and an external apical ring spaced from the distal rim for sewing to the external ventricle wall, the upstream end of the graft extending through the cannula portion and being wrapped around the distal rim to lie against the exterior of the cannula portion and attach to the apical ring.

25. The inflow conduit of claim 24, wherein the tubular graft body is a knitted fabric.

26. The inflow conduit of claim 24, wherein the tubular graft body is a polyethylene terephthalate fabric.

27. The inflow conduit of claim 24, wherein the tubular graft body is a fabric having a biocompatible sealant impregnated therein.

28. The inflow conduit of claim 27, wherein the sealant is bovine gelatin.

29. The inflow conduit of claim 27, wherein the sealant is bovine collagen.

30. The inflow conduit of claim 24, further including an external support secured to an external surface of the tubular graft body.

31. The inflow conduit of claim 24, wherein the tubular graft body is made of PTFE.

32. The inflow conduit of claim 31, wherein the PTFE is closed structured to resist tissue ingrowth from the exterior of the tubular graft body.

33. The inflow conduit of claim 32, further including a plurality of PTFE reinforcement members integrally formed on the external surface of the tubular graft body.

34. An implantable ventricular assist device, comprising:
   an inflow conduit including:
      a flexible tubular graft body having an upstream end and a downstream end, the body having a substantially smooth inner surface for enhanced flow-through of blood with a minimum of surface-induced turbulence;
      a ventricular attachment structure to which the upstream end of the body connects; and
      a coupling fitting on the downstream end of the body;
   an implantable pumping portion in flow communication with the inflow conduit; and
   an outflow conduit in flow communication with the pumping portion.

35. The device of claim 34, wherein the tubular graft body is a knitted fabric having a biocompatible sealant impregnated therein.

36. The device of claim 34, wherein the tubular graft body is made of closed structured PTFE to resist tissue ingrowth from the exterior of the tubular graft body.

37. The device of claim 34, wherein the outflow conduit includes a tubular graft body having a convoluted construction.

* * * * *